(12) United States Patent
Audenaert et al.

(10) Patent No.: US 8,440,779 B2
(45) Date of Patent: May 14, 2013

(54) CARBODIIMIDE COMPOUND AND COMPOSITIONS FOR RENDERING SUBSTRATES OIL AND WATER REPELLENT

(75) Inventors: Frans A. Audenaert, Kaprijke (BE); Chetan P. Jariwala, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 465 days.

(21) Appl. No.: 10/982,107

(22) Filed: Nov. 4, 2004

(65) Prior Publication Data

US 2006/0094851 A1    May 4, 2006

(51) Int. Cl.
*C08G 18/10* (2006.01)
*C07C 251/00* (2006.01)

(52) U.S. Cl.
USPC ............ 528/75; 528/48; 528/60; 528/72; 560/26; 560/115; 560/158; 560/334

(58) Field of Classification Search ........ 560/26, 560/115, 158, 334; 528/48, 60, 72, 75
See application file for complete search history.

(56) References Cited

U.S. PATENT DOCUMENTS

| | | | |
|---|---|---|---|
| 2,803,615 A | 8/1957 | Ahlbrecht | |
| 2,941,966 A * | 6/1960 | Campbell | 521/155 |
| 2,941,983 A | 6/1960 | Smeltz | |
| 2,941,988 A | 6/1960 | Wolf | |
| 3,282,905 A * | 11/1966 | Raynolds et al. | 526/245 |
| 3,660,360 A | 5/1972 | Ray-Chaudhuri | |
| 3,862,989 A | 1/1975 | Hansen | |
| 3,896,251 A | 7/1975 | Landucci | |
| 4,024,178 A | 5/1977 | Landucci | |
| 4,085,137 A | 4/1978 | Mitsch et al. | |
| 4,148,844 A * | 4/1979 | Von Bonin et al. | 528/392 |
| 4,215,205 A | 7/1980 | Landucci | |
| 4,215,405 A | 7/1980 | Brunner et al. | |
| 4,266,040 A * | 5/1981 | Lin | 521/90 |
| 4,540,497 A * | 9/1985 | Chang et al. | 428/375 |
| 4,668,726 A | 5/1987 | Howells | |
| 4,742,140 A | 5/1988 | Greenwood et al. | |
| 5,132,028 A | 7/1992 | Nagase et al. | |
| 5,276,175 A * | 1/1994 | Dams et al. | 560/27 |
| 5,350,795 A * | 9/1994 | Smith et al. | 524/507 |
| 5,725,789 A * | 3/1998 | Huber et al. | 252/8.62 |
| 5,817,249 A * | 10/1998 | Audenaert et al. | 252/8.61 |
| 5,876,617 A | 3/1999 | Sato et al. | |
| 6,121,372 A | 9/2000 | Yamamoto et al. | |
| 6,126,849 A | 10/2000 | Yamana et al. | |
| 6,204,342 B1 * | 3/2001 | Nava | 525/440.02 |
| 6,329,491 B1 * | 12/2001 | Mormile et al. | 528/49 |
| 6,525,127 B1 | 2/2003 | Jariwala et al. | |
| 6,730,807 B1 | 5/2004 | Haberle et al. | |
| 6,737,489 B2 | 5/2004 | Linert et al. | |
| 2003/0220462 A1 | 11/2003 | Porzio et al. | |

FOREIGN PATENT DOCUMENTS

| | | |
|---|---|---|
| DE | 2 310 801 | 9/1973 |
| DE | 199 54 500 | 5/2001 |
| EP | 0 436 327 | 2/1995 |
| EP | 0 526 976 | 1/1997 |
| EP | 0 805 172 | 11/1997 |
| EP | 0 713 863 | 4/2000 |
| EP | 1 329 548 | 7/2003 |
| EP | 1 505 110 | 2/2005 |
| JP | 59-115354 A | 7/1984 |
| JP | 2002-187932 | 7/2002 |
| WO | WO 03/100159 | 12/2003 |

OTHER PUBLICATIONS

K Wagner et al., Angew. Chem. Int. Ed. Engl., vol. 20, p. 819-830 (1981).
S. R. Sandler et al., Org. Functional Group Prep., vol. 2, p. 205-222 (1971).
A Williams et al., Chem. Rev., vol. 81, p. 589-636 (1981).
T. W. Campbell et al. in J. Org. Chem., 28, 2069 (1963).
Blocked isocyanates III.: Part. A, Mechanisms and chemistry by Douglas Wicks and Zeno W. Wicks Jr., *Progress in Organic Coatings*, 36 (1999), pp. 14-172.
Test Method 22-1996, published in the 2001 Technical Manual of the American Association of Textile Chemists and Colorists (AATCC).

\* cited by examiner

*Primary Examiner* — Michael L Leonard
(74) *Attorney, Agent, or Firm* — Robert W. Sprague

(57) ABSTRACT

The invention relates to a carbodiimide compound or mixture of carbodiimide compounds derived from a carbodiimidization reaction of at least one oligomer having at least one isocyanate group and comprising at least two repeating units deriving from one or more ethylenically unsaturated monomers.

14 Claims, No Drawings

CARBODIIMIDE COMPOUND AND COMPOSITIONS FOR RENDERING SUBSTRATES OIL AND WATER REPELLENT

1. FIELD OF THE INVENTION

The invention relates to a carbodiimide compound or mixture of carbodiimide compounds. The invention further relates to compositions comprising said carbodiimide compound or mixture of carbodiimide compounds and a fluorinated compound. The invention also relates to a method of imparting oil and water repellency properties to substrates.

2. BACKGROUND OF THE INVENTION

Compositions for making substrates, in particular fibrous substrates, such as textiles, oil- and water repellent have been long known in the art. Fluorochemical compounds have been well known as being highly effective in providing oil and water repellency to substrates and in particular textile substrates. For example, the fluorochemical composition may be based on fluorochemical acrylates or methacrylates that are derived from the polymerization of an acrylate or methacrylate monomer that has a fluorinated group and optionally one or more non-fluorinated monomers. Such compositions have been described in for example U.S. Pat. No. 3,660,360, U.S. Pat. No. 5,876,617, U.S. Pat. No. 4,742,140, U.S. Pat. No. 6,121,372 and U.S. Pat. No. 6,126,849 and EP 1 329 548.

Additives have been employed to assist in the oil and water repellency of fluorochemical treating agents. U.S. Pat. No. 4,215,405 teaches that water and oil repellency, which is durable to laundering and dry-cleaning is conferred on fabrics by application of a blend of a fluoroaliphatic vinyl polymer and a carbodiimide.

Fluorochemicals are generally expensive. Therefore, hydrocarbon additives, also called extenders, have been developed in order to reduce cost. Modified synthetic resins, waxes, melamines, paraffin emulsions and similar products have been used as extenders.

U.S. Pat. No. 5,132,028 discloses compositions for imparting water and oil repellency to fabrics such as silk said compositions containing a fluorochemical-type, water and oil repellent agent, a carbodiimide, and at least one component selected from the group consisting of plasticizer, metal alcoholate or ester, zirconium salt, alkylketene dimer, aziridine, and alkenyl succinic anhydride.

EP 0 713 863 discloses carbodiimide compounds obtainable from a reaction mixture comprising an isocyanate compound and a monofunctional alcohol in a non-reactive solvent in the presence of a suitable catalyst, characterized in that the isocyanate compound and the monofunctional alcohol, except for the hydroxy group, are free from isocyanate reactive hydrogen atoms and the monofunctional alcohol is a branched aliphatic alcohol containing at least 8 carbon atoms, and to compositions comprising a fluorochemical oil and water repellent agent and said carbodiimide compound.

Water-based fluorochemical compositions are generally preferred from an environmental point of view. In many commercially available aqueous fluorochemical compositions the fluorochemical compound is dispersed in water with the aid of a surfactant. Such compositions have been found to present problems in certain application methods. In particular, in an application where the fluorochemical composition is applied by contacting the substrate with the composition in a bath and then guiding the substrate through a set of rolls, deposition may occur on the rolls after some time of applying the composition to the substrate. This is undesirable as it will require the application to be interrupted to clean the rolls which adds to the manufacturing cost of a treated substrate. This behavior is further influenced by the nature of the fluorochemical composition as well as the nature of the substrate being treated, some substrates and fluorochemical compositions causing the problem more quickly to occur than others. The problem can be reduced by increasing the amount of surfactant in the composition. However, increasing the surfactant level has been found to adversely affect the repellency performance of the composition.

Accordingly, it would be desirable to reduce or even eliminate the aforementioned problem. Preferably a solution to the problem will be environmentally friendly and cost effective. Preferably, the oil- and/or water repellency properties that can be obtained on a substrate with the composition should not be adversely affected when reducing or eliminating the problem of roll deposit. It would further be desirable to find a new extender in particular an extender that is capable of improving the efficiency of the fluorine treatment in a water-based system. It would further be desirable to provide a composition and a process for conferring both static and especially dynamic water repellency onto fibrous substrates without the aforementioned problems associated with roll deposit.

3. BRIEF DESCRIPTION

In one aspect, the invention relates to a carbodiimide compound or mixture of carbodiimide compounds derived from a carbodiimidization reaction of at least one oligomer having at least one isocyanate group and comprising at least two repeating units deriving from one or more ethylenically unsaturated monomers.

In a further aspect, the invention relates to a method of making the aforementioned carbodiimide compound or mixture of carbodiimide compounds.

In still a further aspect, the invention relates to a carbodiimide compound or mixture wherein one or more of the carbodiimide compounds can be represented by the formula (I):

$$Q^1\text{-}X^1\text{—CONH-}(A^1\text{-}(N\!\!=\!\!C\!\!=\!\!N)_q)_m\text{-}A^2\text{-NHCOX}^2\text{-}Q^2 \qquad (I)$$

wherein $X^1$ and $X^2$ each independently represents O, S or NH, $A^1$ and $A^2$ each independently represents the residue of an organic di- or triisocyanate compound obtained by removing the isocyanate groups therefrom, q is 1 or 2, m has a value of 1 to 20 and $Q^1$ and $Q^2$ are selected from a hydrocarbon group that may contain one or more catenary or non-catenary hetero-atoms, a partially or fully fluorinated hydrocarbon group group that may contain one or more catenary or non-catenary hetero-atoms and functional groups corresponding to any of the following formulas:

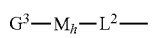
(A)

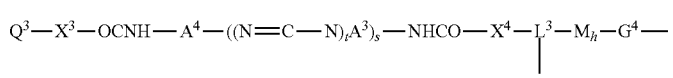
(B)

-continued $$Q^3-X^3-OCNH-A^4-((N{=}C-N)_tA^3)_s-NHCO-X^4-L^4- \quad (C)$$

$$G^4-M_h-L^2-X^3-OCNH-A^4-((N{=}C-N)_tA^3)_s-NHCO-X^4-L^4- \quad (D)$$

$$G^4-M_h-L^2-X^3-OCNH-A^4-((N{=}C-N)_tA^3)_s-NHCO-X^4-\underset{|}{L^3}-M_h-G^4- \quad (E)$$

wherein $G^3$ and $G^4$ each independently represents an end group, $M_h$ represents two or more repeating units deriving from one or more ethylenically unsaturated monomers, $L^2$ represents an organic divalent linking group, $Q^3$ represents a hydrocarbon group that may contain one or more catenary or non-catenary hetero-atoms or a partially or fully fluorinated hydrocarbon group that may contain one or more catenary or non-catenary hetero-atoms, $A^3$ and $A^4$ each independently represents the residue of an organic di- or triisocyanate compound obtained by removing the isocyanate groups therefrom, $X^3$ and $X^4$ each independently represents O, S or NH, s has a value of 1 to 20 and t is 1 or 2, $L^3$ represents an organic trivalent linking group and $L^4$ represents a hydrocarbon group that may optionally contain one or more catenary or non-catenary hetero-atoms or a partially or fully fluorinated hydrocarbon group that may contain one or more catenary or non-catenary hetero-atoms; and wherein at least one $Q^1$ and $Q^2$ corresponds to a group of formula (A), (B), (D) or (E).

In still a further aspect, the invention relates to a composition comprising a fluorinated compound and a carbodiimide compound or mixture of carbodiimide compounds derived from a carbodiimidization reaction of at least one oligomer having at least one isocyanate group and comprising at least two repeating units deriving from one or more ethylenically unsaturated monomers.

In yet a further aspect, the invention pertains to a method of treatment of a substrate, in particular a fibrous substrate, with an aforementioned composition, to render the substrate water and/or oil repellent. In particular, the compositions have been found to be suitable for use in an application method where the substrate is guided through rolls.

It has been found that the carbodiimide compound or mixture of carbodiimide compounds of the present invention can act as excellent extenders in the treatment of substrates, thus typically allowing more efficient use of the more expensive fluorinated compounds. The compositions comprising the carbodiimide compound or mixture of carbodiimide compounds and a fluorinated compound generally provide effective static and/or dynamic water repellency onto substrates.

4. DETAILED DESCRIPTION

According to a particular embodiment, the carbodiimide compound or mixture of carbodiimide compounds of the present invention can be prepared in a three step reaction although it will generally not be required to separate reaction products after the individual steps, i.e. the reaction may be carried out in three steps in a single reactor. In a first step, a functionalized oligomer having at least two repeating units, is prepared which, in a second step, is reacted to form an oligomer having at least one isocyanate group. In a third step said oligomer is further reacted to form a carbodiimide. With the term 'functionalized oligomer' is meant that an oligomer is prepared that contains a functional group capable of reacting with an isocyanate.

In a first step, a functionalized oligomer having at least two repeating units can be prepared by free radical oligomerization of one or more ethylenically unsaturated monomers, typically non-fluorinated ethylenically unsaturated monomers. Examples of ethylenically unsaturated monomers include those represented by the general formula (II):

$$R_h-C(R){=}CR_2 \quad (II)$$

wherein $R_h$ represents H, Cl or a hydrocarbon group that may contain one or more catenary (i.e; in-chain, bonded only to carbon) or non-catenary hetero-atoms and wherein each R being the same or different represents H, a lower alkyl of 1 to 4 carbon atoms, Cl or Br.

The term 'hydrocarbon group' in connection with the present invention, means any substantially fluorine-free organic moiety that contains hydrogen and carbon, and optionally, one or more substituents.

Suitable ethylenically unsaturated monomers are known and are generally commercially available. Examples of such compounds include the general classes of ethylenic compounds capable of free-radical polymerization, such as, for example, allyl esters such as allyl acetate and allyl heptanoate; alkyl vinyl ethers or alkyl allyl ethers such as cetyl vinyl ether, dodecylvinyl ether, 2-chloroethylvinyl ether, ethylvinyl ether; unsaturated acids such as acrylic acid, methacrylic acid, alpha-chloro acrylic acid, crotonic acid, maleic acid, fumaric acid, itaconic acid and their anhydrides and esters such as vinyl, allyl, methyl, butyl, isobutyl, hexyl, heptyl, 2-ethyl-hexyl, cyclohexyl, lauryl, stearyl, isobornyl, octadecyl, hexadecyl or alkoxy ethyl acrylates and methacrylates; alpha-beta unsaturated nitriles such as acrylonitrile, methacrylonitrile, 2-chloroacrylonitrile, 2-cyanoethyl acrylate, alkyl cyanoacrylates; alpha, beta-unsaturated carboxylic acid derivatives such as allyl alcohol, allyl glycolate, acrylamide, methacrylamide, n-diisopropyl acrylamide, diacetoacrylamide, N,N-diethylaminoethylmethacrylate, N-t-butylamino ethyl methacrylate; styrene and its derivatives such as vinyl toluene, alpha-methylstyrene, alpha-cyanomethyl styrene; lower olefinic hydrocarbons which contain halogen such as ethylene, propylene, isobutene, 3-chloro-1-isobutene, isoprene, and allyl or vinyl halides such as vinyl and vinylidene chloride. Other useful monomers include monomers that contain a urethane group, such as the reaction product of 2-hydroxy-ethyl(meth)acrylate with a monofunctional isocyanate, such as octadecyl isocyanate. Particular suitable monomers include those selected from the group consisting of octadecyl(meth)acrylate, hexadecyl(meth)acrylate, methylmethacrylate, butyl(meth)acrylate, isobutyl (meth)acrylate and isobornyl(meth)acrylate, ethylhexyl methacrylate, urethane containing (meth)acrylate as described above, and mixtures thereof.

The free radical oligomerization is typically carried out in the presence of mono- or difunctional hydroxy- or amino functionalized chain transfer agents, in order to prepare mono- or difunctionalized oligomers respectively. Examples of mono functional chain transfer agents include those selected from 2-mercaptoethanol, 3-mercapto-2-butanol, 3-mercapto-2-propanol, 3-mercapto-1-propanol and 2-mercapto-ethylamine. A particularly suitable monofunctional chain transfer agent is 2-mercaptoethanol. Examples of difunctional chain transfer agents include those having two hydroxyl or amino groups or a hydroxy and amino group. A particular suitable example of a difunctional chain transfer agent is 3-mercapto-1,2-propanediol.

The functionalized oligomer should generally comprise a sufficient number of repeating units to render the portion oligomeric. The oligomer suitably comprises from 2 to 40, in particular from 2 to 20 repeating units derived from one or more ethylenically unsaturated monomers. According to a particular embodiment, the oligomer has 3 to 15 repeating units. According to another embodiment, the oligomer has between 4 and 15 repeating units.

In order to prepare the functionalized oligomer, a free-radical initiator may be used to initiate the oligomerization. Free-radical initiators include those known in the art and include in particular azo compounds, such as 2,2'-azobi-sisobutyronitrile (AIBN) and 2,2'-azobis(2-cyanopentane) and the like, hydroperoxides such as cumene, t-butyl, and t-amylhydroperoxide, peroxyesters such as t-butylperbenzoate and di-t-butylperoxyphtalate, diacylperoxides such as benzoyl peroxide and lauroyl peroxide.

The oligomerization reaction can be carried out in any solvent suitable for organic free-radical reactions. Particularly suitable solvents are solvents that do not interfere with the isocyanate reactions in the second and the third step to form the carbodiimide. The reactants can be present in the solvent at any suitable concentration, e.g., from about 5 percent to about 90 percent by weight based on the total weight of the reaction mixture. Examples of suitable solvents include aliphatic and alicyclic hydrocarbons (e.g., hexane, heptane, cyclohexane), ethers (e.g., diethylether, glyme, diglyme, diisopropyl ether), esters (e.g., ethyl acetate, butyl acetate), ketones (e.g., acetone, methylethyl ketone, methyl isobutyl ketone) and mixtures thereof.

The oligomerization reaction can be carried out at any temperature suitable for conducting a free-radical oligomerization reaction. Particular temperature and solvents for use can be easily selected by those skilled in the art based on considerations such as the solubility of reagents, the temperature required for the use of a particular initiator, molecular weight desired and the like. While it is not practical to enumerate a particular temperature suitable for all initiators and all solvents, generally suitable temperatures are between about 30° C. and about 150° C.

In a second step, an oligomer having at least one isocyanate group is prepared by a condensation reaction of the functionalized oligomer with an excess of a polyisocyanate, i.e. a di- or triisocyanate. Generally, the second reaction step is also conducted in the presence of one or more further isocyanate reactive compounds. Such further isocyanate reactive compounds are typically compounds containing one or two isocyanate-reactive groups and include mono- and difunctional alcohols, thiols and amines. The further isocyanate reactive compounds are generally non-fluorinated but can be partially or fully fluorinated as well. A single compound or a mixture of different compounds may be used. Examples include alcanols, such as methanol, ethanol, n-propylalcohol, isopropyl alcohol, n-butyl alcohol, isobutyl alcohol, t-butyl alcohol, n-amyl alcohol, t-amyl alcohol, 2-ethylhexanol, glycidol, (iso)stearylalcohol, behenyl alcohol, branched long chain alkanols, such as Guerbet alcohols (2-alkyl alkanols having C-14 to C-24 alkyl chains, available from Henkel), alcohols comprising poly(oyalkylene) groups, such as eg. methyl or ethyl ether of polyethyleneglycol, hydroxyl-terminated methyl or ethyl ether of random or block copolymer of ethyleneoxide and/or propyleneoxide and polysiloxane group containing alcohols. Further examples include diols, such as 1,4-butanediol, 1,6-hexanediol, 1-10-decanediol, 4,4'-isopropylidene diphenol (Bisphenol A); polyester diols, such as polycaprolactone diol, fatty acid dimer diols and poly(oxy) alkylenediols with an oxyalkylene group having 2 to 4 carbon atoms, such as $—OCH_2CH_2—$, $—O(CH_2)_4—$, $—OCH_2CH_2CH_2—$, $—OCH(CH_3)CH_2—$ and $—OCH(CH_3)CH(CH_3)—$ (preferably the oxyalkylene units in said poly(oxyalkylene) being the same, as in polypropyleneglycol or present as a mixture), ester diols, such as glycerolmonostearate and polysiloxane group containing diols.

Further suitable isocyanate reactive compounds include amino group containing compounds, such as amino-terminated polyethyleneoxide or propyleneoxide or copolymers thereof, amino-terminated methyl or ethylethers of polyethyleneoxide or polypropyleneoxide or copolymers thereof and amino group terminated polysiloxanes. Fluorinated isocyanate reactive compounds that may be used include for example partially fluorinated or perfluorinated polyethers that have one or two isocyanate reactive groups such as hydroxyl groups, amino groups and thiol groups. Still further, a fluorinated isocyanate reactive compound that can be used is a partially or fully fluorinated aliphatic compound having one or two isocyanate reactive groups such as hydroxyl groups, amino groups and thiol groups. Examples of the latter include perfluorinated aliphatic mono-alcohols having 3, 4 or upto 14 carbon atoms.

Still further suitable isocyanate reactive compounds include thiol group containing compounds, such as 1,4-butanedithiol, 1,6-hexanedithiol.

Particularly suitable further isocyanate reactive compounds include monofunctional alcohols, such as (iso)stearylalcohol and C-18 2-alkyl alkanols; ester diols, such as glycerol monostearate, amino- or hydroxy group containing polysiloxanes and mixtures thereof.

The isocyanate reactive compounds may be used alone or in combination. The isocyanate reactive compound can be present up to about 50 mole % based on the total amount of isocyanate functionalities.

Polyisocyanates for use in accordance with the present invention include aliphatic and aromatic di- and triisocyanates. Examples of diisocyanates include 4,4'-methylenediphenylenediisocyanate (MDI), 2,4-toluenediisocyanate, 2,6-toluene diisocyanate, o, m, and p-xylylene diisocyanate, 4,4'-diisocyanatodiphenylether, 3,3'-dichloro-4,4'-diisocyanatodiphenylmethane, 4,4'-diphenyldiisocyanate, 4,4'-diisocyanatodibenzyl, 3,3'-dimethoxy-4,4'-diisocyanatodiphenyl, 3,3'-dimethyl-4,4'-diisocyanatodiphenyl, 2,2'-dichloro-5,5'-dimethoxy-4,4'-diisocyanato diphenyl, 1,3-diisocyanatobenzene, 1,2-naphthylene diisocyanate, 4-chloro-1,2-naphthylene diisocyanate, 1,3-naphthylene diisocyanate, and 1,8-dinitro-2,7-naphthylene diisocyanate; alicyclic diisocyanates such as 3-isocyanatomethyl-3,5,5-trimethylcyclohexylisocyanate; 3-isocyanatomethyl-3,5,5-trimethylcyclohexylisocyanate; aliphatic diisocyanates such as 1,6-hexamethylenediisocyanate, 2,2,4-trimethyl-1,6-hexamethylenediisocyanate, and 1,2-ethylenediisocyanate; cyclic diisocyanates such as isophorone diisocyanate (IPDI) and dicyclohexylmethane-4,4'-diisocyanate. Examples of triisocyanates include aliphatic triisocyanates such as 1,3,6-hexamethylenetriisocyanate and aromatic triisocyanates such as polymethylenpolyphenylisocyanate (PAPI, Voranate™), DESMODUR™R (tri-(4-isocyanatophenyl)-methane, available from Bayer) and DESMODUR™ L (available from Bayer). Also useful are isocyanates containing internal isocyanate derived moieties such as biuret-containing triisocyanates such as that available from Bayer as DESMODUR™N-100 and isocyanurate-containing triisocyanates such as that available from Huls AG, Germany, as IPDI-1890 and Desmodur N-3300, available from Bayer.

Particular suitable polyisocyanates include aromatic polyisocyanates such as MDI and 2,4-toluenediisocyanate and aliphatic polyisocyanates, such as hexamethylene diisocyanate, Desmodur™N, Desmodur™W and Desmodur™N-3300.

The oligomer having at least one isocyanate group can be prepared by a condensation reaction, carried out under conventional conditions well-known to those skilled in the art. The condensation reaction is preferably carried out under dry conditions in a polar solvent such as ethyl acetate, acetone, methyl isobutyl ketone, and the like. Suitable reaction temperatures will be easily determined by those skilled in the art based on the particular reagents, solvents, and catalysts being used. While it is not practical to enumerate particular temperatures suitable for all situations, generally suitable temperatures are between about room temperature and about 120° C.

In a particular embodiment of the present invention, the oligomer having at least one isocyanate group may be represented by formula (III):

  (III)

wherein $M_h$ represents two or more repeating units deriving from one or more ethylenically unsaturated monomers, $G^1$ and $G^2$ each independently represents an end group and wherein at least one of the end groups comprises an isocyanate group. In one embodiment of the invention, one of the end groups is free of isocyanate groups and the other group comprises one or two isocyanate groups. In a particular embodiment, one of the end groups is free of isocyanate groups and the other group comprises a group of the formula:

-L¹-CO—NH—Z—NCO wherein $L^1$ represents O, or NH and Z represents an aliphatic or aromatic group.

In a third step, the carbodiimide compound or mixture of carbodiimide compounds can be formed by a condensation reaction of the oligomers having at least one isocyanate group, in the presence of suitable catalysts as described, for example by K Wagner et al., Angew. Chem. Int. Ed. Engl., vol 20, p 819-830 (1981); by S. R. Sandler et al., Org. Functional Group Prep., vol 2, p 205-222 (1971) and by A Williams et al., Chem. Rev., vol 81, p 589-636 (1981). The preparation of urethane containing or urethane terminated polycarbodiimides has been described in e.g. U.S. Pat. No. 2,941,983 and by T. W. Campbell et al. in J. Org. Chem., 28, 2069 (1963). Representative examples of suitable catalysts are described in e.g. U.S. Pat. No. 2,941,988, U.S. Pat. No. 3,862,989 and U.S. Pat. No. 3,896,251. Examples include 1-ethyl-3-phospholine, 1-ethyl-3-methyl-3-phospholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the organic polyisocyanate being used. A concentration range of 0.05-5 parts of catalyst per 100 parts of oligomer having at least one isocyanate group is generally suitable. The carbodiimidization reaction may involve further isocyanate compounds other than the isocyanate containing oligomer. Such further isocyanate compounds include mono-isocyanates as well as polyisocyanates such as those described above.

In a particular embodiment according to the present invention the carbodiimide compound can be represented by the formula (I):

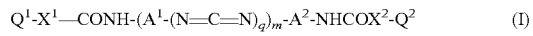  (I)

wherein $X^1$ and $X^2$ each independently represents O, S or NH, $A^1$ and $A^2$ each independently represents the residue of an organic di- or triisocyanate compound obtained by removing the isocyanate groups therefrom, q is 1 or 2, m has a value of 1 to 20 and $Q^1$ and $Q^2$ are selected from a hydrocarbon group that may contain one or more catenary or non-catenary hetero-atoms, a partially or fully fluorinated hydrocarbon group that may contain one or more catenary or non-catenary hetero-atoms and functional groups corresponding to any of the following formulas:

 (A)

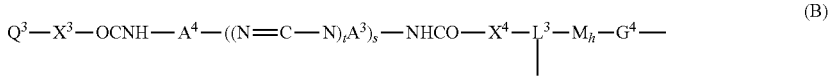 (B)

 (C)

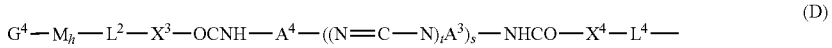 (D)

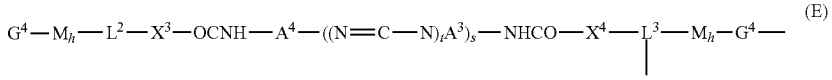 (E)

wherein $G^3$ and $G^4$ each independently represents an end group, $M_h$ represents two or more repeating units deriving from one or more ethylenically unsaturated monomers, $L^2$ represents an organic divalent linking group, $Q^3$ represents a hydrocarbon group that may contain one or more catenary or non-catenary hetero-atoms or a partically or fully fluorinated hydrocarbon group that may contain one or more catenary or non-catenary hetero-atoms, $A^3$ and $A^4$ each independently represents the residue of an organic di- or triisocyanate compound obtained by removing the isocyanate groups therefrom, $X^3$ and $X^4$ each independently represents O, S or NH, s has a value from 1 to 20 and t is 1 or 2, $L^3$ represents an organic trivalent linking group and $L^4$ represents hydrocarbon group that may optionally contain one or more catenary or non-catenary hetero-atoms or a partially or fully fluorinated hydrocarbon group that may contain one or more catenary or non-catenary hetero-atoms; and wherein at least one of $Q^1$ and $Q^2$ corresponds to a group of formula (A), (B), (D) or (E).

The groups $A^1$, $A^2$, $A^3$ and $A^4$ (hereinafter collectively referred to as "A-groups") each independently represent the residue of an organic di- or triisocyanate compound obtained by removing the isocyanate groups therefrom. The A-groups may be the same or different. When A is trivalent, derived from triisocyanates, branched or crosslinked polycarbodiimides can result. Different A-groups may be used together to give slight branching in order to modify properties. Substituents may be present in A provided they contain no isocyanate-reactive hydrogen atoms. Particularly suitable groups A are unsubstituted organic linking groups, such as e.g.

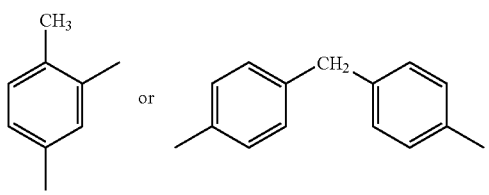

The endgroups $G^3$ and $G^4$ typically represent hydrogen or the residue of the initiator used to prepare the functionalized oligomer.

The linking groups $L^2$ and $L^3$ respectively represent an organic divalent or trivalent linking group. Examples thereof include divalent or trivalent aliphatic including linear branched or cyclic aliphatic groups or aromatic groups. The linking groups $L^2$ and $L^3$ generally comprise between 1 and 30 carbon atoms, for example between 2 and 12 carbon atoms.

The terminal group $Q^3$ represents a hydrocarbon group, optionally partially or fully fluorinated, that may contain one or more catenary or non-catenary hetero-atoms. $Q^3$ generally has between 1 and 50 carbon atoms. The terminal group $Q^3$ may for example represent the residue of a monofunctional isocyanate reactive compound, for example of an isocyanate reactive compound as described above, obtained by removal of the isocyanate reactive group. Examples for $Q^3$ include monovalent aliphatic including linear branched or cyclic aliphatic groups or aromatic groups, a partially or fully fluorinated aliphatic group or a partially or fully fluorinated polyether group. Particular useful examples for end groups $Q^3$ include linear or branched aliphatic terminal moieties of at least 8 carbon atoms.

Linking group $L^4$ represents an aromatic or aliphatic hydrocarbon group that may optionally contain one or more caternary or non-catenary hetero-atoms. The linking group $L^4$ may for example represent the residue of a difunctional isocyanate reactive compound, for example as described above, obtained after removing the isocyanate reactive groups therefrom. Examples thereof include divalent aliphatic groups including linear branched or cyclic aliphatic groups or aromatic groups as well as partially or fully fluorinated aliphatic groups. The aliphatic groups may contain one or more caternary or non-catenary heteroatoms such as oxygen and nitrogen. Particular suitable example of $L^4$ include:

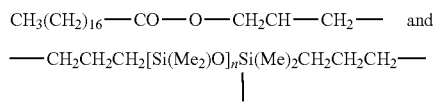

and

It will further be appreciated by one skilled in the art that the preparation of the carbodiimide results in a mixture of compounds and accordingly, general formula (III) should be understood as representing a mixture of compounds whereby the indices q, m, t and s in formula (III) represent the molar amount of the corresponding unit in such mixture.

After completion of the carbodiimidization reaction, the final reaction mixture may be dispersed in water using a surfactant or mixture of surfactants in an amount sufficient to stabilize the dispersion. A typical dispersion will contain water in an amount of about 70 to 20000 parts by weight based on 100 parts by weight of carbodiimide compound or mixture of carbodiimide compounds. The surfactant or mixture of surfactants is preferably present in an amount of about 1 to 25 parts by weight, preferably about 5 to 15 parts by weight based on 100 parts by weight of the carbodiimide compound or mixture of carbodiimide compounds. Conventional cationic, non-ionic, anionic and Zwitterionic surfactants and mixtures of nonionic and charged surfactants are suitable.

Commercially available surfactants that can be used include Arquad™ T-50, Arquad™ MCB-50, Ethoquad™ C-12 and Ethoquad™ 18-25 from Akzo-Nobel and Tergitol™ TMN-6 and Tergitol™ 15S30, available from Rohm & Haas Suitable fluorinated compounds for use in the composition according to the invention include any of the fluorochemical group-containing organic compounds including polymeric and oligomeric compounds known in the art to impart water and oil repellency to substrates. These polymeric and oligomeric fluorinated compounds typically comprise one or more fluorochemical groups that contain a perfluorinated carbon chain having from 3 to about 20 carbon atoms, typically from about 4 to about 14 carbon atoms. These fluorochemical groups can contain straight chain, branched chain, or cyclic fluorinated alkylene groups or any combination thereof. The fluorochemical groups are preferably free of polymerizable olefinic unsaturation but can optionally contain catenary heteroatoms such as oxygen, divalent or hexavalent sulfur, or nitrogen. Fully-fluorinated groups are preferred, but hydrogen or chlorine atoms can also be present as substituents, provided that no more than one atom of either is present for every two carbon atoms. It is additionally preferred that any fluorochemical group contain from about 40% to about 80% fluorine by weight, more preferably about 50% to about 78% fluorine by weight. The terminal portion of the group is generally fully-fluorinated, preferably containing at least 7 fluorine atoms. Perfluorinated aliphatic groups (i.e., those of the formula $C_nF_{2n+1}$—) are the most preferred fluorochemical groups.

Representative examples of suitable fluorinated compounds include fluorochemical urethanes, ureas, esters, ethers, alcohols, epoxides, allophanates, amides, amines (and salts thereof), acids (and salts thereof), carbodimides, guanidines, oxazolidinones, isocyanurates, biurets, acrylate and methacrylate homopolymers and copolymers, and mixtures thereof.

In one particular embodiment, the fluorinated compound comprises a fluorinated polymer comprising one or more repeating units derived from a fluorinated monomer corresponding to the formula (IV):

$$R_f-L^5C(R)=CR_2 \quad\quad (IV)$$

wherein $R_f$ represents a fluorinated aliphatic group or a perfluorinated polyether group, $L^5$ represents an organic divalent linking group, and each R independently represents hydrogen or a lower alkyl group having 1 to 3 carbon atoms.

The fluorinated aliphatic group $R_f$ in the fluorinated monomer is a typically a perfluorinated aliphatic group. It can be straight chain, branched chain, or cyclic or combinations thereof. The $R_f$ radical has at least 3 and up to 18 carbon atoms, preferably 3 to 14, especially 4 to 10 carbon atoms, and preferably contains about 40% to about 80% fluorine by weight, more preferably about 50% to about 79% fluorine by weight. The terminal portion of the $R_f$ radical is a perfluorinated moiety, which will preferably contain at least 7 fluorine atoms, e.g., $CF_3CF_2CF_2-$, $(CF_3)_2CF-$, $F_5SCF_2-$. The preferred $R_f$ radicals are those perfluorinated aliphatic radicals of the formula $C_nF_{2n+1}-$ where n is 3 to 18, particularly 4 to 10. Compounds wherein the $R_f$ radical is a $C_4F_9-$ are generally more environmentally acceptable than compounds where the $R_f$ radical consists of a perfluorinated group with more carbon atoms.

The $R_f$ group can also be a perfluorinated polyether group. The perfluorinated polyether group $R_f$ can include linear, branched, and/or cyclic structures, that may be saturated or unsaturated, and substituted with one or more oxygen atoms. It is preferably a perfluorinated group (i.e., all C—H bonds are replaced by C—F bonds). More preferably, it includes perfluorinated repeating units selected from the group of $-(C_nF_{2n})-$, $-(C_nF_{2n}O)-$, $-(CF(Z))-$, $-(CF(Z)O)-$, $-(CF(Z)C_nF_{2n}O)-$, $-(C_nF_2CF(Z)O)-$, $-(CF_2CF(Z)O)-$, and combinations thereof. In these repeating units Z is a perfluoroalkyl group, an oxygen-substituted perfluoroalkyl group, a perfluoroalkoxy group, or an oxygen-substituted perfluoroalkoxy group, all of which can be linear, branched, or cyclic, and preferably have about 1 to about 9 carbon atoms and 0 to about 4 oxygen atoms. The terminal groups can be $(C_nF_{2n+1})-$ or $(C_nF_{2n+1}O)-$. In these repeating units or terminal groups, n is 1 or more, and preferably about 1 to about 4. Particularly preferred approximate average structures for a perfluoropolyether group include $C_3F_7O(CF(CF_3)CF_2O)_pCF(CF_3)-$ and $CF_3O(C_2F_4O)_pCF_2-$ wherein an average value for p is 1 to about 50. As synthesized, these compounds typically include a mixture of polymers. The approximate average structure is the approximate average of the mixture of polymers.

The organic divalent linking group $L^5$ in the above formula (IV) links the perfluorinated aliphatic group or the perfluorinated polyether group $R_f$ to the free radical polymerizable group and is a generally non-fluorinated organic linking groups. The linking group can be a chemical bond, but preferably contains from 1 to about 20 carbon atoms and may optionally contain oxygen, nitrogen, or sulfur-containing groups or a combination thereof. The linking group is preferably free of functional groups that substantially interfere with free-radical oligomerization (e.g., polymerizable olefinic double bonds, thiols, and other such functionality known to those skilled in the art). Examples of suitable organic divalent linking groups include:
*—COQ'-$R^1$-Q"-CO—, *—COO—$CH_2$—CH(OH)—$R^1$-Q'-CO—, *-L'-Q'-CONH-L"-, *—$R^1$-Q'-CO—*—COQ'-$R^1$—, —$R^1$—, *—COQ'-$R^1$-Q'-, *—$SO_2NR^a$—$R^1$-Q'-, *—$SO_2NR^a$—$R^1$— and *—$SO_2NR^a$—$R^1$-Q'-CO—, wherein Q' and Q" independently represent O or $NR^a$, $R^a$ is hydrogen or an alkyl group of 1 to 4 carbon atoms, $R^1$ represents a linear, cyclic or branched alkylene group that may be interrupted by one or more heteroatoms such as O or N, L' and L" each independently represent a non-fluorinated organic divalent linking group including for example an alkylene group, a carbonyl group, a carbonamido alkylene group and/or carboxy alkylene group, and indicates the position where the linking group is attached to the group $R_f$ in formula (IV).

Fluorinated monomers $R_f$-$L^5$-C(R)=$CR_2$ as described above and methods for the preparation thereof are known and disclosed, e.g., in U.S. Pat. No. 2,803,615. Examples of such compounds include general classes of fluorochemical acrylates, methacrylates, vinyl ethers, and allyl compounds containing fluorinated sulfonamido groups, acrylates or methacrylates derived from fluorochemical telomer alcohols, acrylates or methacrylates derived from fluorochemical carboxylic acids, and perfluoroalkyl acrylates or methacrylates as disclosed in EP-A-526 976.

Perfluoropolyetheracrylates or methacrylates are described in U.S. Pat. No. 4,085,137.

Particularly suitable examples of fluorinated monomers include:

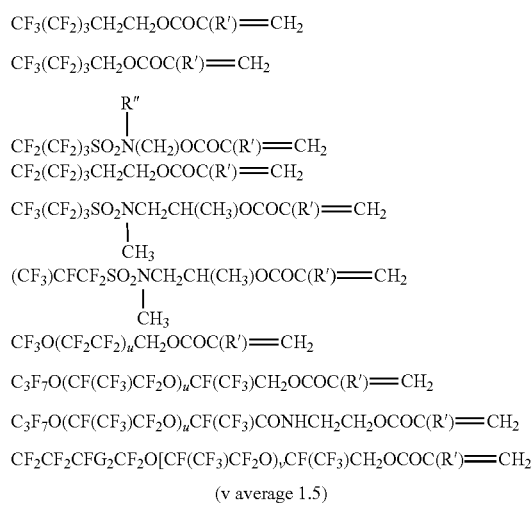

(v average 1.5)

wherein R' represents hydrogen or methyl, R" represents methyl, ethyl or n-butyl and u is about 1 to 25.

The fluorinated monomer according to formula (IV) or mixture thereof is typically used in amounts such that the amount of the corresponding units thereof in the polymer is between 10 and 97 mole %, preferably between 25 and 97 mole %, more preferably between 25 mole % and 85 mole %, most preferably between 25 mole % and 75 mole %.

The fluorinated monomer according to formula (IV) is generally copolymerized with one or more non-fluorinated monomers. In one embodiment, at least part of the non-fluorinated monomers is selected from chlorine containing monomers such as vinyl chloride and vinylidene chloride. Repeating units of such chlorine containing monomers, when present, are preferably contained in the fluorinated polymer in an amount between 3 and 75 mole %.

Further non-fluorinated comonomers, other than the chlorine containing monomers referred to above, include hydrocarbon group containing monomers such as monomers that can be represented by formula (V):

wherein $R_h$ represents an aliphatic group having 4 to 30 carbon atoms, $L^6$ represents an organic divalent linking group and E represents an ethylenically unsaturated group. The hydrocarbon group is preferably selected from the group consisting of a linear, branched or cyclic alkyl group, an aralkyl group, an alkylaryl group and an aryl group. Further non-fluorinated monomers include those wherein the hydrocarbon group in formula (V) includes oxyalkylene groups or substituents, such as hydroxy groups and/or cure sites.

Examples of non-fluorinated comonomers include hydrocarbon esters of an α,β-ethylenically unsaturated carboxylic acid. Examples include n-butyl(meth)acrylate, isobutyl (meth)acrylate, octadecyl(meth)acrylate, lauryl(meth)acrylate, cyclohexyl (meth)acrylate, cyclodecyl (meth)acrylate, isobornyl (meth)acrylate, phenyl (meth)acrylate, benzyl (meth)acrylate, adamantyl (meth)acrylate, tolyl (meth)acrylate, 3,3-dimethylbutyl (meth)acrylate, (2,2-dimethyl-1-methyl)propyl (meth)acrylate, cyclopentyl (meth)acrylate, 2-ethylhexyl (meth)acrylate, t-butyl (meth)acrylate, cetyl (meth)acrylate, stearyl (meth)acrylate, behenyl (meth)acrylate, isooctyl (meth)acrylate, n-octyl (meth)acrylate, 4-ethylcyclohexyl (meth)acrylate, 2-ethoxyethyl methacrylate and tetrahydropyranyl acrylate. Further non-fluorinated comonomers include allyl esters such as allyl acetate and allyl heptanoate; alkyl vinyl ethers or alkyl allyl ethers such as cetyl vinyl ether, dodecylvinyl ether, ethylvinyl ether; unsaturated acids such as acrylic acid, methacrylic acid, alpha-chloro acrylic acid, crotonic acid, maleic acid, fumaric acid, itaconic acid and their anhydrides and their esters such as vinyl, allyl, methyl, butyl, isobutyl, hexyl, heptyl, 2-ethylhexyl, cyclohexyl, lauryl, stearyl, isobornyl or alkoxy ethyl acrylates and methacrylates; alpha-beta unsaturated nitriles such as acrylonitrile, methacrylonitrile, 2-chloroacrylonitrile, 2-cyanoethyl acrylate, alkyl cyanoacrylates; alpha,beta-unsaturated carboxylic acid derivatives such as allyl alcohol, allyl glycolate, acrylamide, methacrylamide, n-diisopropyl acrylamide, diacetoneacrylamide, aminoalkyl (meth)acrylates such as N,N-diethylaminoethylmethacrylate, N-t-butylaminoethylmethacrylate; alkyl(meth)acrylates having an ammonium group such as (meth)acrylates of the formula $X^-R_3N^+—R^a—C(O)—CR^1=CH_2$ wherein $X^-$ represents an anion such as e.g. a chloride anion, R represents hydrogen or an alkyl group and each R may be the same or different, $R^a$ represents an alkylene and $R^1$ represents hydrogen or methyl; styrene and its derivatives such as vinyltoluene, alpha-methylstyrene, alpha-cyanomethyl styrene; lower olefinic hydrocarbons which can contain halogen such as ethylene, propylene, isobutene, 3-chloro-1-isobutene, butadiene, isoprene, chloro and dichlorobutadiene and 2,5-dimethyl-1,5-hexadiene, hydrocarbon monomers comprising (poly)oxyalkylene groups including (meth)acrylates of a polyethylene glycol, (meth)acrylates of a block copolymer of ethylene oxide and propylene oxide, (meth)acrylates of amino- or diamino terminated polyethers and (meth)acrylates of methoxypolyethyleneglycols and hydrocarbon monomers comprising a hydroxyl group include hydroxylgroup containing (meth) acrylates, such as hydroxyethyl(meth)acrylate and hydroxypropyl(meth)acrylate.

In a particular embodiment of the invention, the fluorinated polymer comprising units deriving from a monomer according to formula (IV) further includes units having one or more cure sites. These units will typically derive from corresponding comonomers that include one or more cure sites. By the term 'cure site' is meant a functional group that is capable of engaging in a reaction with the substrate to be treated. Examples of cure sites include acid groups such as carboxylic acid groups, hydroxy groups, amino groups and isocyanate groups or blocked isocyanate groups. Examples of comonomers from which a cure site unit may derive include (meth) acrylic acid, maleic acid, maleic anhydride, allyl methacrylate, hydroxybutyl vinyl ether, N-hydroxymethyl (meth) acrylamide, N-methoxymethyl acrylamide, N-butoxymethyl acrylamide, N-isobutoxymethyl acrylamide, glycidylmethacrylate and α,α dimethyl m. isopropenyl benzyl isocyanate. Other examples include polymerizable urethanes, that can be obtained by the reaction of a polymerizable mono-isocyanate with an isocyanate blocking agent or by the reaction of a di- or poly-isocyanate and a hydroxy or amino-functionalized acrylate or methacrylate and an isocyanate blocking agent. Isocyanate blocking agents are compounds that upon reaction with an isocyanate group yield a group that is unreactive at room temperature with compounds that at room temperature normally react with an isocyanate but which group at elevated temperature reacts with isocyanate reactive compounds. Generally, at elevated temperature the blocking group will be released from the blocked (poly)isocyanate compound thereby generating the isocyanate group again which can then react with an isocyanate reactive group. Blocking agents and their mechanisms have been described in detail in "Blocked isocyanates III.: Part. A, Mechanisms and chemistry" by Douglas Wicks and Zeno W. Wicks Jr., *Progress in Organic Coatings*, 36 (1999), pp. 14-172.

The blocked isocyanate may be aromatic, aliphatic, cyclic or acyclic and is generally a blocked di- or triisocyanate or a mixture thereof and can be obtained by reacting an isocyanate with a blocking agent that has at least one functional group capable of reacting with an isocyanate group. Preferred blocked isocyanates are blocked polyisocyanates that at a temperature of less than 150° C. are capable of reacting with an isocyanate reactive group, preferably through deblocking of the blocking agent at elevated temperature. Preferred blocking agents include arylalcohols such as phenols, lactams such as ε-caprolactam, δ-valerolactam, γ-butyrolactam, oximes such as formaldoxime, acetaldoxime, methyl ethyl ketone oxime, cyclohexanone oxime, acetophenone oxime, benzophenone oxime, 2-butanone oxime or diethyl glyoxime. Particular examples of comonomers having a blocked isocyanate group as the cure site include the reaction product of a di-isocyanate, 2-hydroxyethyl(meth)acrylate and 2-butanone oxime or the reaction product of a di-isocyanate, a mono(meth)acrylate of a polyethylene glycol and 2-butanone oxime and the reaction product of a triisocyanate, 1 equivalent of 2-hydroxyethyl(meth)acrylate and 2 equivalents of 2-butanone oxime and the reaction product of α,α-dimethyl m. isopropenyl benzyl isocyanate with 2-butanone oxime. In yet a further embodiment in connection with the present invention, the fluorochemical compound used in the composition is an alkylated fluorochemical oligomer as disclosed in U.S. Pat. No. 6,525,127. The alkylated fluorochemical oligomers disclosed in this US patent comprise:
(i) a fluorochemical oligomeric portion comprising an aliphatic backbone with a plurality of fluoroaliphatic groups attached thereto, each fluoroaliphatic group having a fully fluorinated terminal group and each independently linked to a carbon atom of the aliphatic backbone through an organic linking group;
(ii) an aliphatic moiety having at least 12 carbon atoms; and
(iii) a linking group which links the fluorochemical oligomeric portion to the aliphatic moiety.

The compositions comprising a fluorinated compound and a carbodiimide or mixture of carbodiimides can be prepared by blending aqueous dispersions of the carbodiimide or mixture of carbodiimide and fluorinated compound. In order to improve fixing of the composition of the invention to a substrate, it is sometimes advantageous to include in the dispersion certain additives, polymers, thermo-condensable products and catalysts capable of promoting interaction with the substrate. Among these are the condensates or precondensates of urea or melamine with formaldehyde (sometimes referred to herein as resins) and glyoxal resins. Particular suitable additives and amounts thereof can be selected by those skilled in the art.

The amount of the treating composition applied to a substrate should generally be chosen so that sufficiently high or desirable water and oil repellencies are imparted to the substrate surface, said amount usually being such that 0.01% to 5% by weight, preferably 0.05% to 2% by weight, based on the weight of the substrate, of water repellent composition (fluorinated compound and carbodiimide compound or mixture of carbodiimide compounds) is present on the treated substrate. The amount which is sufficient to impart desired repellency can be determined empirically and can be increased as necessary or desired.

The carbodiimide compound or mixture of carbodiimide compounds is generally present in the treating composition in an amount sufficient to improve the fluorine efficiency of the fluorinated compound. "Improvement in fluorine efficiency" as used herein designates that improved or equal repellency properties are obtained when part of the fluorinated compound, preferably 10 to 50% by weight of fluorinated compound, is replaced by the carbodiimide. Generally, the carbodiimide compound or mixture of carbodiimide compounds is present in an amount of about 5 to about 500, preferably about 10 to about 200, and most preferably about 25 to about 100 parts by weight based on 100 parts by weight of the fluorinated compound.

The composition of this invention can be applied using conventional application methods and can particularly be used as an aqueous dispersion. A dispersion will generally contain water, an amount of composition effective to provide repellent properties to a substrate treated therewith, and a surfactant in an amount effective to stabilize the dispersion. Water is preferably present in an amount of about 70 to about 20000 parts by weight based on 100 parts by weight of the composition of the invention. The surfactant is preferably present in an amount of about 1 to about 25 parts by weight, preferably about 5 to about 10 parts by weight, based on 100 parts by weight of the inventive composition. Conventional cationic, nonionic, anionic, Zwitterionic surfactants or mixtures thereof are suitable.

In order to effect treatment of a substrate, the dispersion can be sprayed on the substrate or the substrate can be immersed in the dispersion and agitated until it is saturated. The saturated substrate can then be run through a padder/roller to remove excess dispersion. The composition in accordance with the present invention is particularly suitable for use in an application method where the composition is applied to the substrate by contacting the substrate with the composition in a bath that contains the composition and wherein the substrate is guided over one or more rolls. Typically, such rolls are configured so as to squeeze excess treatment composition from the substrate.

Following application of the composition to the substrate, the substrate will generally be dried. The substrate may be dried at ambient conditions by leaving the substrate exposed to air for a certain period of time. Good and effective repellency properties may be obtained with compositions according to the invention even when drying at ambient conditions (generally at 20 to 30° C.). Alternatively, the substrate may be exposed to heat subsequent to the application of the composition to accelerate drying of the substrate and/or to cause curing of the applied composition if desired or necessary. When exposed to a heat temperature, the substrate may be guided through an oven and the temperature of heat treatment may be between 100 and 200° C., typically between 120 and 180° C.

The amount of the treating composition applied to a substrate in accordance with this invention is chosen so that sufficiently high or desirable water and oil repellencies are imparted to the substrate surface, said amount usually being such that 0.01% to 5% by weight, preferably 0.05% to 2% by weight, based on the weight of the substrate, of water repellent composition (fluorinated compound and carbodiimide) is present on the treated substrate. The amount which is sufficient to impart desired repellency can be determined empirically and can be increased as necessary or desired.

The substrates treated by the water and oil repellency imparting composition of this invention are not especially limited and include, e.g. textile fabrics, fibres, non-wovens, leather, paper, carpet, plastic, wood, metal, glass, concrete and stone. Preferred are textile fabrics, fibres and non-wovens.

The invention is further illustrated with reference to the following examples without however the intention to limit the invention thereto.

EXAMPLES

Formulation and Treatment Procedure

Treatment baths were formulated containing a defined amount of the fluorinated compound and carbodiimide. Unless otherwise indicated, treatments were applied to the test substrates by padding at a concentration to provide 0.3% or 0.6% solids of the treatment composition (based on fabric weight and indicated as SOF (solids on fabric)). Drying and curing was done at 160° C. for 1.5 minutes.

Test Methods

Spray Rating (SR)

The spray rating of a treated substrate is a value indicative of the dynamic repellency of the treated substrate to water that impinges on the treated substrate. The repellency was measured by Test Method 22-1996, published in the 2001 Technical Manual of the American Association of Textile Chemists and Colorists (AATCC), and was expressed in terms of a 'spray rating' of the tested substrate. The spray rating was obtained by spraying 250 ml water on the substrate from a height of 15 cm. The wetting pattern was visually rated using a 0 to 100 scale, where 0 means complete wetting and 100 means no wetting at all.

Oil Repellency (OR)

The oil repellency of a substrate was measured by the American Association of Textile Chemists and Colorists (AATCC) Standard Test Method No. 118-1983, which test was based on the resistance of a treated substrate to penetration by oils of varying surface tensions. Treated substrates resistant only to Nujol® mineral oil (the least penetrating of the test oils) were given a rating of 1, whereas treated substrates resistant to heptane (the most penetrating of the test liquids) were given a rating of 8. Other intermediate values were determined by use of other pure oils or mixtures of oils, as shown in the following table.

Standard Test Liquids

| AATCC Oil Repellency Rating Number | Compositions |
|---|---|
| 1 | Nujol ® |
| 2 | Nujol ®/n-Hexadecane 65/35 |
| 3 | n-Hexadecane |
| 4 | n-Tetradecane |
| 5 | n-Dodecane |
| 6 | n-Decane |
| 7 | n-Octane |
| 8 | n-Heptane |

Bundesmann Test

The impregnating effect of rain on treated substrates was determined using the Bundesmann Test Method (DIN 53888). In this test, the treated substrates were subjected to a simulated rainfall, while the back of the substrate was being rubbed. The appearance of the upper exposed surface was checked visually after 1, 5 and 10 minutes and was given a rating between 1 (complete surface wetting) and 5 (no water remains on the surface). Besides the observation of the wetting pattern, also the water absorption (% abs) was measured. Well-treated samples gave low absorption results.

Water Repellency Test (WR)

The water repellency (WR) of a substrate was measured using a series of water-isopropyl alcohol test liquids and was expressed in terms of the "WR" rating of the treated substrate. The WR rating corresponded to the most penetrating test liquid which did not penetrate or wet the substrate surface after 15 seconds exposure. Substrates which were penetrated by or were resistant only to 100% water (0% isopropyl alcohol), the least penetrating test liquid, were given a rating of 0, whereas substrates resistant to 100% isopropyl alcohol (0% water), the most penetrating test liquid, were given a rating of 10. Other intermediate ratings were calculated by dividing the percent isopropylalcohol in the test liquid by 10, e.g., a treated substrate resistant to a 70%/30% isopropyl alcohol/water blend, but not to an 80%/20% blend, would be given a rating of 7.

Laundering Procedure

The procedure set forth below was used to prepare treated substrate samples designated in the examples below as 5HL IR (5 Home Launderings—ironing).

A 230 g sample of generally square, 400 cm$^2$ to about 900 cm$^2$ sheets of treated substrate was placed in a washing machine along with a ballast sample (1.9 kg of 8 oz fabric in the form of generally square, hemmed 8100 cm$^2$ sheets). A commercial detergent ("Sapton", available from Henkel, Germany, 46 g) was added and the washer was filled to high water level with hot water (40° C.+/−3° C.). The substrate and ballast load were washed five times using a 12-minute normal wash cycle followed by five rinse cycles and centrifuging. The samples were not dried between repeat cycles. After drying, the samples were pressed using an iron with the temperature set for the fiber of the substrate.

Abbreviations

Ethoquad™ C-12: cocobis(2-hydroxyethyl)methyl ammonium chloride (75% in H$_2$O) from Akzo-Nobel
iBMA: isobutyl methacrylate
IPDI: isophorone diisocyanate
GMS: Glycerol monostearate
ODA/HDA: a 50/50 blend of octadecylacrylate and hexadecane acrylate, available as Photomer 4818F from Cognis,
ODA: octadecyl acrylate, available from Osaka.
4,4'-MDI: 4,4' methylene diphenyl diisocyanate, available from BASF AG.
MIBK: methyl isobutyl ketone (4-methyl 2-pentanone)
MMA: methyl methacrylate
ODI: octadecyl isocyanate
ODMA: octadecyl or stearyl methacrylate
VCL$_2$: vinylidene chloride
CPPO: camphene phenyl phosphine oxide catalyst
Tergitol™ TMN-6: trimethylnonane polyoxyethylene (6 EO) surfactant from Rohm & Haas
Tergitol™ 15S30: C12-14 alkyl polyoxyethylene(30 EO) surfactant from Rohm & Haas
PCD: polycarbodiimide
Prisorine 3515: Iso-stearyl alcohol, obtained from Uniquema
RBU: roll build-up
PES/CO (2681.4): polyester/cotton 65/35 obtained from Utexbel N.V., Ronse, Belgium
PAμ (7819.4): Polyamide microfiber, style No. 7819.4, obtained from Sofinal, Belgium
PES (0030.1): polyester, style No. 0030.1, obtained from Radici, Italy
PESμ: polyester moss microfiber peach effect (sanded), available from San Laing Surface Fabric co.
PA: polyamide taffeta (190 or 210 yarn fiber) for apparel, available from Sunny Specific Mill
FC: 45% solids aqueous dispersion comprising a fluorochemical acrylate having the following monomer composition $C_4F_9SO_2N(CH_3)CH_2CH_2OCOC(CH_3)=CH_2/VCL_2/$ ODMA (weight ratio: 60/20/20) and an emulsifier system of 2% Ethoquad™ C-12/5.4% Tergitol™ TMN-6 and 3% Tergitol™ 15S30 based on fluorochemical acrylate solids.

Synthesis of Carbodiimide Extenders a. Synthesis of Reference Carbodiimide: 4MDI/Stearyl Alcohol/Isostearyl Alcohol, Further Indicated as c-PCD In a first step the polycarbodiimide was prepared. A 3-necked reaction flask equipped with a thermometer, Dean Stark condenser, mechanical stirrer, heating mantle and nitrogen inlet, was charged with 13.5 g (0.05 eq.) stearyl alcohol, 13.5 g (0.05 eq.) Prisorine 3515 and 167 g MIBK. 50 g MIBK/H$_2$O azeotrope was distilled off via the Dean Stark condenser. After replacing the Dean Stark by a normal reflux condenser, the mixture was cooled to 65° C. and 50 g MDI (0.4 eq.) were added. The reaction mixture was heated for 3 hours at 75° C. Then 5.0 g CPPO (20% solution in dichloromethane) was charged. The reaction mixture was heated for 16 hours at 90° C. FTIR analysis indicated complete conversion.

In a second step, 80 g reaction mixture was emulsified. The PCD solution was dispersed in water containing Ethoquad™ C-12 (2% on solids), Tergitol 15S30 (3% on solids) and Tergitol™ TMN-6 (5.4% solids) using a Branson 450 sonifier. The solvent was stripped off with a Büchi evaporator, using water jet vacuum. A stable, milky dispersion was obtained.

b. Synthesis of 8 MDI/2 Isostearylalcohol/(8ODA/HDA-HSCH$_2$CHOHCH$_2$OH), Further Indicated ad PCD-1

In a first step, functionalized ODA/HDA oligomer was prepared. A 250 ml polymerization bottle was charged with 86.4 g ODA/HDA (267 meq.), 3.6 g 2-mercaptopropane diol (33 meq.), 60 g MIBK and 0.26 g Vazo 67. The mixture was repeatedly degassed using water jet vacuum, followed by breaking the vacuum with nitrogen atmosphere. The polymerization bottle was sealed and run for 20 hours at 75° C. in a pre-heated Launder-o-meter. A clear, very slightly yellow, non-viscous oligomer solution of 60% solids was obtained.

In a second step, a 500 ml 3-necked reaction flask equipped with a thermometer, Dean Stark condenser, mechanical stirrer, heating mantle and nitrogen inlet, was charged with 67.5 g of the ODA/HDA oligomer solution as prepared above (50 meq.), 13.5 g isostearylacohol (50 meq.) and 153 g MIBK. 50 g MIBK/H$_2$O azeotrope was distilled off via the Dean Stark condenser. After replacing the Dean Stark by a normal reflux condenser, the mixture was cooled to 65° C. and 50 g MDI (400 meq.) were added. The reaction mixture was heated for 30 min at 75° C.

In a third step, the carbodiimization reaction was done. 5.0 g camphene phenyl phosphine oxide catalyst (CPPO, 20% solution in dichloromethane) was added. The reaction mixture was heated overnight at 95° C., yielding a slightly hazy, non-viscous solution. FTIR analysis indicated complete conversion.

The reaction mixture was emulsified as follows: 300 g polycarbodiimide solution as prepared above was heated to 65° C. and added to a hot aqueous solution of Ethoquad™ C-12 (2% on solids), Tergitol 15S30 (3% on solids) and Tergitol™ TMN-6 (5.4% solids). 199 g water was added. The mixture was emulsified with 2 stage lab Manton-Gaulin at 220/20 bar (2 passes). The solvent was stripped off with a Büchi evaporator, using water jet vacuum. A stable, milky dispersion of 21.9% solids was obtained.

c. Synthesis of 4 MDI/Isostearylalcohol/(8iBMA-HSCH$_2$CH$_2$OH), Further Indicated as PCD-2

In a first step, iBMA oligomer was prepared. A 500 ml polymerization bottle was charged with 94.7 g iBMA (667 meq.), 6.5 g 2-mercaptoethanol (83.3 meq.), 67.4 g MIBK and 0.284 g V-59. The mixture was repeatedly degassed using water jet vacuum, followed by breaking the vacuum with nitrogen atmosphere. The polymerization bottle was sealed and run for 16 hours at 75° C. in a pre-heated Launder-o-meter. A clear, colorless, non-viscous oligomer solution of 60% solids was obtained.

In a second step, a 3-necked reaction flask equipped with a thermometer, Dean Stark condenser, mechanical stirrer, heating mantle and nitrogen inlet, was charged with 60.7 g of the iBMA oligomer solution as prepared above (30 meq.), 8.1 g isostearylacohol (30 meq.) and 138.4 g MIBK. 50 g MIBK/H$_2$O azeotrope was distilled off via the Dean Stark condenser. After replacing the Dean Stark by a normal reflux condenser, the mixture was cooled to 65° C. and 30.3 g MDI (240 meq.) were added. The reaction mixture was heated for 2 hours at 75° C.

In a third step, the carbodiimidization reaction was carried out after the addition of 3.0 g camphene phenyl phosphine oxide catalyst (CPPO, 20% solution in dichloromethane). The reaction mixture was heated for 16 hours at 95° C., yielding a slightly hazy, non-viscous solution. FTIR analysis indicated complete conversion.

150 g reaction mixture was emulsified according to the procedure as described for the PCD-1.

Polycarbodiimides PCD-3 to PCD-5 as given in table 1, were prepared according to the same procedure.

TABLE 1

Composition of Carbodiimides (mole ratio)

| PCD | Composition |
| --- | --- |
| PCD-2 | 4 MDI/isostearyl alcohol/(8 iBMA-HSCH$_2$CH$_2$OH) |
| PCD-3 | 4 MDI/0.5 isostearyl alcohol/0.5 stearylalcohol/(8 iBMA-HSCH$_2$CH$_2$OH) |
| PCD-4 | 4 MDI/0.5 isostearyl alcohol/0.5 behenyl alcohol/(8 iBMA-HSCH$_2$CH$_2$OH) |
| PCD-5 | 4 MDI/isostearyl alcohol/(4 ODA-HSCH$_2$CH$_2$OH) | d. Synthesis of 5 MDI/2(4 MMA-HSCH$_2$CH$_2$OH)/GMS), Further Indicated as PCD-6

In a first step, a 500 ml polymerization bottle was charged with 80 g MMA (0.8 eq.), 15.6 g 2-mercaptoethanol (0.2 eq.), 63.7 g MIBK and 0.24 g V-59. The mixture was repeatedly degassed using water jet vacuum, followed by breaking the vacuum with nitrogen atmosphere. The polymerization bottle was sealed and run for 16 hours at 75° C. in a pre-heated Launder-o-meter. A clear, colorless, non-viscous oligomer solution of 60% solids was obtained.

In a second step, a 3-necked reaction flask equipped with a thermometer, Dean Stark condenser, mechanical stirrer, heating mantle and nitrogen inlet, was charged with 47.8 g MMA oligomer solution (0.06 eq.) as prepared in the first step, 40.74 g glycerol monostearate (0.06 eq.) and 144.4 g MIBK. 50 g MIBK/H$_2$O azeotrope was distilled off via the Dean Stark condenser. After replacing the Dean Stark by a normal reflux condenser, the mixture was cooled to 65° C. and 37.5 g MDI (0.3 eq.) was added. The reaction mixture was heated for 2 hours at 75° C., yielding a clear solution.

In a third step, 3.75 g CPPO was charged. The reaction mixture was heated for 16 hours at 95° C. FTIR analysis indicated complete conversion.

150 g reaction mixture was emulsified according to the procedure described for reference PCD-1.

Carbodiimides PCD-7 to PCD-10, with compositions as given in table 2, were prepared according to the same procedure.

TABLE 2

Composition of Carbodiimides PCD-6 to PCD-10 (mole ratio)

| PCD | Composition |
| --- | --- |
| PCD-6 | 5 MDI/glycerol mono stearate/2 (4 MMA-HSCH$_2$CH$_2$OH) |
| PCD-7 | 12 MDI/(4 ODA/HDA-HSCH$_2$CH$_2$OH)/2 GMS |
| PCD-8 | 12 MDI/(4 ODA/HDA-MeFBSEA-HSCH$_2$CH$_2$OH)/2 GMS |
| PCD-9 | 12 MDI/(2 ODA/HDA-(2 ODI-HEMA)-HSCH$_2$CH$_2$OH)/2 GMS |
| PCD-10 | 12 MDI/((4 ODI-HEMA)-HSCH$_2$CH$_2$OH)/2 GMS | e. Synthesis of 12 MDI/Isostearylalcohol/(8 ODA/HDA-HSCH$_2$CH$_2$OH)/2 GMS, Further Indicated as PCD-11

In a first step, an ODA/HDA oligomer (8 ODA/HDA-HSCH$_2$CH$_2$OH) was prepared as described for the synsthesis of ODA/HDA oligomer (8 ODA/HDA-HSCH$_2$CHOHCH$_2$OH), using mercaptoethanol instead of mercaptopropanediol.

In a second step, a 3-necked reaction flask equipped with a thermometer, Dean Stark condenser, mechanical stirrer, heating mantle and nitrogen inlet, was charged with 26.7 g ODA/HDA oligomer (8 ODA/HDA-HSCH$_2$CH$_2$OH) solution (10 meq.), 2.7 g isostearylalcohol (10 meq.), 7.16 g GMS (40 meq) and 82.9 g MIBK. 50 g MIBK/H$_2$O azeotrope was distilled off via the Dean Stark condenser. After replacing the Dean Stark by a normal reflux condenser, the mixture was cooled to 65° C. and 30 g MDI (240 meq.) were added. The reaction mixture was heated for 2 hours at 75° C.

In a third step, 3.0 g camphene phenyl phosphine oxide catalyst (CPPO, 20% solution in dichloromethane) was charged. The reaction mixture was heated for 16 hours at 95° C., yielding a slightly hazy, non-viscous solution. FTIR analysis indicated complete conversion.

150 g reaction mixture was emulsified according to the procedure as described for the PCD-1.

Polycarbodiimide 12 MDI/isostearylalcohol/(8 ODA/HDA-HSCH$_2$CH$_2$OH)/4 GMS, further indicated as PCD-12 was prepared according to the same procedure.

Examples 1 to 28 and Comparative Examples C-1 to C-4

In examples 1 to 28, substrates were treated with a blends of fluorinated compound (FC) (0.18% SOF) and various carbodiimides (at 0.12% SOF) as given in table 3 and using the general treatment procedure. Comparative examples C-1 to C-4 were made the same way, but only using FC (0.3% SOF). The treated fabrics were tested for oil and water repellency. The results are given in table 3.

TABLE 3

| Ex No. | PCD | Initial OR | WR | SR | Bundesmann 1' | 5' | 10' | %ABS | 5HL Ironing OR | SR |
|---|---|---|---|---|---|---|---|---|---|---|
| PAμ |
| 1 | PCD-1 | 3 | 3 | 100 | 5 | 3 | 2 | 30.9 | 1 | 80 |
| 2 | PCD-11 | 3 | 3 | 100 | 5 | 2 | 1 | 32.3 | 0 | 80 |
| 3 | PCD-12 | 3 | 3 | 90 | 5 | 3 | 2 | 32.1 | 1 | 80 |
| 4 | PCD-7 | 3 | 3 | 100 | 4 | 2 | 1 | 28.4 | 1 | 80 |
| 5 | PCD-8 | 2 | 3 | 100 | 4 | 2 | 2 | 30.9 | 0 | 80 |
| 6 | PCD-9 | 2 | 3 | 90 | 4 | 2 | 2 | 31.3 | 1 | 80 |
| 7 | PCD-10 | 2 | 3 | 90 | 3 | 2 | 1 | 30.4 | 0 | 80 |
| C-1 | / | 2 | 3 | 100 | 4 | 2 | 1 | 31.9 | 0 | 50 |
| PES |
| 8 | PCD-1 | 2 | 3 | 100 | 3 | 2 | 1 | 15.9 | 0 | 70 |
| 9 | PCD-11 | 2 | 3 | 100 | 4 | 3 | 2 | 18.2 | 0 | 80 |
| 10 | PCD-12 | 2 | 3 | 100 | 4 | 3 | 2 | 15.6 | 0 | 70 |
| 11 | PCD-7 | 2 | 3 | 100 | 3 | 2 | 2 | 18.6 | 0 | 70 |
| 12 | PCD-8 | 2 | 3 | 100 | 4 | 2 | 2 | 15.3 | 0 | 70 |
| 13 | PCD-9 | 2 | 3 | 100 | 2 | 1 | 1 | 18.1 | 1 | 70 |
| 14 | PCD-10 | 2 | 3 | 100 | 3 | 1 | 1 | 18.3 | 1 | 80 |
| C-2 | / | 2 | 3 | 100 | 2 | 1 | 1 | 23.6 | 0 | 50 |
| PES/CO |
| 15 | PCD-1 | 3 | 3 | 100 | 3 | 2 | 2 | 23.8 | 1 | 85 |
| 16 | PCD-11 | 2 | 3 | 100 | 4 | 2 | 2 | 24.9 | 1 | 85 |
| 17 | PCD-12 | 3 | 3 | 100 | 4 | 3 | 2 | 24.0 | 1 | 80 |
| 18 | PCD-7 | 2 | 3 | 100 | 4 | 2 | 1 | 23.2 | 1 | 85 |
| 19 | PCD-8 | 2 | 3 | 100 | 4 | 2 | 1 | 25.9 | 1 | 80 |
| 20 | PCD-9 | 2 | 3 | 100 | 2 | 1 | 1 | 29.9 | 1 | 75 |
| 21 | PCD-10 | 1 | 3 | 100 | 3 | 1 | 1 | 27.5 | 2 | 80 |
| C-3 | / | 3 | 4 | 100 | 2 | 1 | 1 | 27.7 | 1 | 50 |
| Cotton |
| 22 | PCD-1 | 2 | 3 | 90 | 3 | 1 | 1 | 36.9 | 1 | 80 |
| 23 | PCD-11 | 2 | 3 | 90 | 2 | 1 | 1 | 37.2 | 0 | 80 |
| 24 | PCD-12 | 1 | 3 | 90 | 3 | 1 | 1 | 36.0 | 0 | 80 |
| 25 | PCD-7 | 2 | 3 | 90 | 2 | 1 | 1 | 35.1 | 1 | 85 |
| 26 | PCD-8 | 2 | 3 | 90 | 2 | 1 | 1 | 35.7 | 1 | 80 |
| 27 | PCD-9 | 2 | 3 | 90 | 2 | 1 | 1 | 36.8 | 0 | 80 |
| 28 | PCD-10 | 1 | 3 | 90 | 2 | 1 | 1 | 37.7 | 0 | 80 |
| C-4 | / | 2 | 3 | 90 | 1 | 1 | 1 | 38.7 | 0 | 50 |

Examples 29 to 44 and Comparative Examples C-5 to C-7

In examples 29 to 44 the same experiment was repeated with blends of FC (0.18% solids) and various polycarbodi-imides (at 0.12% solids) as given in table 4. Treatment was done by padding so as to give 0.18% SOF FC and 0.12% SOF PCD. Comparative examples C-5 to C-7 were made with only FC (0.3% SOF), no polycarbodiimide was added. After drying and curing at 160° C. for 3 minutes, the oil and water repellency properties were measured. The results are given in table 4.

TABLE 4

Properties of substrates treated with blend of FC and polycarbodiimide

| Ex No. | PCD | Initial OR | WR | SR | Bundesmann 1' | 5' | 10' | %ABS | 5HL Ironing OR | SR |
|---|---|---|---|---|---|---|---|---|---|---|
| PES |
| 29 | PCD-5 | 1.5 | 2.5 | 100 | 5 | 4 | 3 | 10.3 | 0 | 85 |
| 30 | PCD-2 | 1.5 | 2.5 | 100 | 4 | 2 | 1 | 16.0 | 0.5 | 90 |
| 31 | PCD-3 | 1.5 | 2.5 | 90 | 5 | 4 | 4 | 8.0 | 0 | 90 |
| 32 | PCD-4 | 1.5 | 2.5 | 100 | 5 | 4 | 4 | 9.7 | 0 | 90 |
| C-5 | / | 2 | 4 | 100 | 2 | 1 | 1 | 16.7 | 0 | 70 |

TABLE 4-continued

Properties of substrates treated with blend of FC and polycarbodiimide

| Ex No. | PCD | Initial OR | WR | SR | Bundesmann 1' | 5' | 10' | %ABS | 5HL Ironing OR | SR |
|---|---|---|---|---|---|---|---|---|---|---|
| PAμ |
| 33 | PCD-5 | 2 | 3 | 90 | 5 | 3 | 2 | 23.6 | 0 | 75 |
| 34 | PCD-2 | 1.5 | 3.5 | 100 | 4 | 2 | 1 | 29.9 | 0.5 | 80 |
| 35 | PCD-3 | 2 | 3.5 | 90 | 4 | 2 | 1 | 29.3 | 0.5 | 80 |
| 36 | PCD-4 | 2.5 | 2.5 | 90 | 5 | 3 | 2 | 28.1 | 0 | 85 |
| C-6 | / | 2 | 3.5 | 100 | 4 | 1 | 1 | 29.9 | 0 | 50 |
| PES/CO |
| 37 | PCD-5 | 2.5 | 3 | 100 | 5 | 3 | 2 | 20.9 | 1 | 80 |
| 38 | PCD-2 | 2 | 3.5 | 100 | 5 | 2 | 1.5 | 20.9 | 0.5 | 80 |
| 39 | PCD-3 | 1.5 | 3 | 100 | 5 | 3 | 1.5 | 23.5 | 0.5 | 90 |
| 40 | PCD-4 | 1.5 | 3 | 100 | 5 | 3 | 2 | 22.5 | 0 | 80 |
| C-6 | / | 2.5 | 3.5 | 100 | 2 | 1 | 1 | 27.1 | 0.5 | 50 |
| Cotton |
| 41 | PCD-5 | 1.5 | 2.5 | 90 | 2 | 1 | 1 | 33.0 | 0 | 75 |
| 42 | PCD-2 | 1 | 3.5 | 90 | 3 | 1 | 1 | 33.1 | 0 | 80 |
| 43 | PCD-3 | 1 | 3.5 | 90 | 2.5 | 1 | 1 | 32.1 | 0 | 80 |
| 44 | PCD-4 | 1 | 3.5 | 90 | 2.5 | 1 | 1 | 34.7 | 0 | 85 |
| C-7 | / | 1 | 3.5 | 90 | 1 | 1 | 1 | 36.8 | 0 | 50 |

Examples 45 and 46 and Comparative Example C-8

Examples 45 and 46 were run to evaluate the roll build up (RBU) during the application of the blends of fluorinated compound and polycarbodiimide having compositions as given in table 5. Therefore, treatment baths were prepared by diluting an amount of product dispersion, corresponding to 45 g solids (60% FC and 40% PCD), to a 5 l bath with tap water and 2 g/l of 60% acetic acid.

A polyamide substrate was run on a Butterworth padder via a continuous loop through the bath containing the blend of fluorinated compound and PCD. Bath stability and RBU were observed during a 1 hour run (speed: 25 m/min; pressure 80 psi). In order to quantify the RBU, a visual rating between 1 (severe RBU) and 5 (no RBU) was given. Comparative example C-8 was made in the same way, but with a bath containing 60% FC and 40% comparative polycarbodiimide c-PCD.

TABLE 5 measurement of RBU

| Ex No | FC + PCD | RBU |
|---|---|---|
| 45 | FC + PCD-6 | 4-5 |
| 46 | FC + PCD-2 | 4 |
| C-8 | FC + cPCD | 1 |

The invention claimed is:

1. Carbodiimide compound or mixture of carbodiimide compounds derived from a carbodiimidization reaction of at least one oligomer having at least one isocyanate group and comprising at least two repeating units deriving from one or more ethylenically unsaturated acrylic monomers; wherein said ethylenically unsaturated acrylic monomers correspond to the general formula:

$$R_h-C(O)-C(R)=CR_2$$

wherein $R_h$ represents H, Cl, or a hydrocarbon group that may contain one or more catenary or non-catenary hetero-atoms and wherein each R being the same or different represents H, a lower alkyl of 1 to 4 carbon atoms, Cl, or Br; and wherein said repeating units are non-fluorinated.

2. Carbodiimide compound or mixture according to claim 1 wherein said carbodiimidization reaction further involves one or more isocyanate compounds other than said oligomer having at least one isocyanate group.

3. Carbodiimide compound or mixture according to claim 2 wherein said further one or more isocyanate compounds are selected from aromatic or aliphatic polyisocyanates.

4. Carbodiimide compound or mixture according to claim 1 wherein said oligomer corresponds to the formula:

$$G^1\text{-}M_h\text{-}G^2$$

wherein $M_h$ represents two or more repeating units deriving from one or more ethylenically unsaturated acrylic monomers, and $G^1$ and $G^2$ each independently represents an end group wherein at least one of said end groups comprises an isocyanate group.

5. Carbodiimide compound or mixture derived from a carbodiimidization reaction of at least one oligomer having at least one isocyanate group and comprising at least two repeating units deriving from one or more ethylenically unsaturated monomers wherein said oligomer corresponds to the formula:

$$G^1\text{-}M_h\text{-}G^2$$

wherein $M_h$ represents two or more repeating units deriving from one or more ethylenically unsaturated monomers corresponding to the general formula:

$$R_h\text{—}C(O)\text{—}C(R)\text{=}CR_2$$

wherein $R_h$ represents H, Cl, or a hydrocarbon group that may contain one or more catenary or non-catenary hetero-atoms and wherein each R being the same or different represents H, a lower alkyl of 1 to 4 carbon atoms, Cl, or Br, and $G^1$ and $G^2$ each independently represents an end group wherein at least one of said end groups comprises an isocyanate group wherein one of said end groups is free of isocyanate groups and wherein the other end group comprises 1 or 2 isocyanate groups; and wherein the repeating units are non-fluorinated.

6. Carbodiimide compound derived from a carbodiimidization reaction of at least one oligomer having at least one isocyanate group and comprising at least two repeating units deriving from one or more ethylenically unsaturated monomers wherein said oligomer corresponds to the formula:

$$G^1\text{-}M_h\text{-}G^2$$

wherein $M_h$ represents two or more repeating units deriving from one or more ethylenically unsaturated monomers corresponding to the general formula:

$$R_h\text{—}C(O)\text{—}C(R)\text{=}CR_2$$

wherein $R_h$ represents H, Cl, or a hydrocarbon group that may contain one or more catenary or non-catenary hetero-atoms and wherein each R being the same or different represents H, a lower alkyl of 1 to 4 carbon atoms, Cl, or Br, and $G^1$ and $G^2$ each independently represents an end group wherein at least one of said end groups comprises an isocyanate group wherein one of said end groups is free of isocyanate groups and the other end group comprises a group of the formula:

$$\text{-}L^1\text{-}CO\text{—}NH\text{—}Z\text{—}NCO$$

wherein $L^1$ represents O or NH, and Z represents an aliphatic or aromatic group; and wherein said repeating units are non-fluorinated.

7. Carbodiimide compound according to claim 1 wherein said oligomer has between 2 and 20 repeating units.

8. Composition comprising a fluorinated compound and a carbodiimide compound or mixture of claim 1.

9. Composition according to claim 8 wherein said fluorinated compound is polymeric compound comprising one or more repeating units deriving from a fluorinated monomer of the formula:

$$R_f\text{-}L^5\text{-}C(R)\text{=}CR_2$$

wherein $R_f$ represents a perfluorinated aliphatic group of 3 or 4 carbon atoms or a perfluorinated polyether group, $L^5$ represents an organic divalent linking group, and each R independently represents H or a lower alkyl group having 1 to 3 carbon atoms.

10. Method of treatment comprising contacting a substrate with a composition of claim 8.

11. Method of treatment according to claim 10 wherein said substrate is selected from the group consisting of textile, leather, carpet, paper and non-wovens.

12. Method of making a carbodiimide compound or mixture of claim 1 comprising reacting at least one oligomer comprising at least two repeating units deriving from one or more ethylenically unsaturated acrylic monomers and having 1 or more isocyanate groups in the presence of a catalyst for causing carbodiimidization of the isocyanate groups.

13. Method of making a carbodiimide compound or mixture derived from a carbodiimidization reaction of at least one oligomer having at least one isocyanate group and comprising at least two repeating units deriving from one or more ethylenically unsaturated monomers comprising reacting at least one oligomer comprising at least two repeating units deriving from one or more ethylenically unsaturated monomers and having 1 or more isocyanate groups in the presence of a catalyst for causing carbodiimidization of the isocyanate groups wherein said oligomer is prepared by (i) a free radical polymerization of one or more ethylenically unsaturated monomers in the presence of a chain transfer agents having one or two isocyanate reactive groups and (ii) reacting a thus obtained functionalized oligomer with a polyisocyanate compound or mixture having on average at least two isocyanate groups;

wherein said ethylenically unsaturated acrylic monomers correspond to the general formula:

$$R_h\text{—}C(O)\text{—}C(R)\text{=}CR_2$$

wherein $R_h$ represents H, Cl, or a hydrocarbon group that may contain one or more catenary or non-catenary hetero-atoms and wherein each R being the same or different represents H, a lower alkyl of 1 to 4 carbon atoms, Cl, or Br; and wherein said repeating units are non-fluorinated.

14. Method according to claim 13 wherein said reaction of said functionalized oligomer with said polyisocyanate compound further involves the co-reaction with one or more further isocyanate reactive compounds other than a functionalized oligomer.

* * * * *

UNITED STATES PATENT AND TRADEMARK OFFICE
CERTIFICATE OF CORRECTION

PATENT NO.        : 8,440,779 B2
APPLICATION NO.   : 10/982107
DATED             : May 14, 2013
INVENTOR(S)       : Frans Audenaert It is certified that error appears in the above-identified patent and that said Letters Patent is hereby corrected as shown below:

In the Specification:

Column 1
Line 17, Delete "oil-" and insert -- oil --, therefor.

Column 2
Line 56, after "hydrocarbon" delete "group".

Columns 1-2
Line 61 (Approx.) (Including Structure),

Delete " $Q^3-X^3-OCNH-A^4-((N=C-N)_tA^3)_s-NHCO-X^4-L^3-M_h-G^4-$ " and insert -- $Q^3-X^3-OCNH-A^4-((N=C=N)_tA^3)_s-NHCO-X^4-L^3-M_h-G^4-$ --, therefor.

Columns 3-4
Line 1, Delete " $Q^3-X^3-OCNH-A^4-((N=C-N)_tA^3)_s-NHCO-X^4-L^4-$ " and insert -- $Q^3-X^3-OCNH-A^4-((N=C=N)_tA^3)_s-NHCO-X^4-L^4-$ --, therefor.

Columns 1-4
Line 2 (Approx.) (Including Structure),

Delete " $G^4-M_h-L^2-X^3-OCNH-A^4-((N=C-N)_tA^3)_s-NHCO-X^4-L^4-$ " and insert -- $G^4-M_h-L^2-X^3-OCNH-A^4-((N=C=N)_tA^3)_s-NHCO-X^4-L^4-$ --, therefor.

Signed and Sealed this
Twenty-fourth Day of September, 2013

Teresa Stanek Rea
*Deputy Director of the United States Patent and Trademark Office*

CERTIFICATE OF CORRECTION (continued)

Columns 3-4
Line 3 (Approx.) (Including Structures),

Delete "  " and insert -- 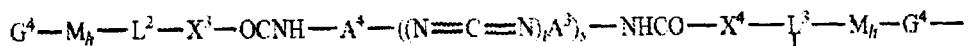 --, therefor.

Column 5
Line 67, Delete "poly(oyalkylene)" and insert -- poly(oxyalkylene) --, therefor.

Column 5,
Line 67, Delete "eg." and insert -- e.g., --, therefor.

Column 2
Line 65, Delete "polymethylenpolyphenylisocyanate" and insert
-- polymethylenepolyphenylisocyanate --, therefor.

Columns 7-8
Line 39 (Approx.) (Including Structure),

Delete " 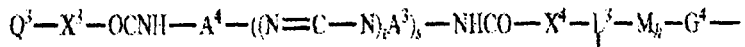 " and insert -- 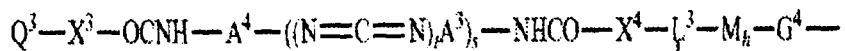 --, therefor.

Columns 7-8
Line 40 (Approx) (Including Structures),

Delete " $Q^3-X^3-OCNH-A^4-((N=C-N)_tA^3)_s-NHCO-X^4-L^4-$ " and insert -- $Q^3-X^3-OCNH-A^4-((N=C=N)_tA^3)_s-NHCO-X^4-L^4-$ --, therefor.

Columns 2-8
Line 41 (Approx.) (Including Structures),

Delete " $G^4-M_h-L^2-X^3-OCNH-A^4-((N=C-N)_tA^3)_s-NHCO-X^4-L^4-$ " and insert -- $G^4-M_h-L^2-X^3-OCNH-A^4-((N=C=N)_tA^3)_s-NHCO-X^4-L^4-$ --, therefor.

Columns 7-8
Line 42 (Approx) (Including Structures),

Delete "$G^4—M_h—L^2—X^3—OCNH—A^4—((N=C—N)_zA^3)_s—NHCO—X^4—L^3—M_h—G^4—$" and insert -- $G^4—M_h—L^2—X^3—OCNH—A^4—((N=C=N)_zA^3)_s—NHCO—X^4—L^3—M_h—G^4—$ --, therefor.

Column 8
Line 56, Delete "partically" and insert -- partially --, therefor.

Column 9
Line 50 (Approx.), Delete "caternary" and insert -- catenary --, therefor.

Column 9
Line 57-58 (Approx.), Delete "caternary" and insert -- catenary --, therefor.

Column 10
Line 25, Delete "Haas" and insert -- Haas. --, therefor.

Column 10
Line 54, Delete "carbodimides," and insert -- carbodiimides, --, therefor.

Column 10
Line 62 (Approx.), Delete "$R_f-L^5C(R)=CR_2$" and insert -- $R_f-L^5-C(R)=CR_3$ --, therefor.

Column 11
Line 66, Delete "and" and insert -- and * --, therefor.

Column 12
Line 33 (Approx.), Delete "$CFG_2$" and insert -- $CF_2$ --, therefor.

Column 13
Line 32, Delete "C(O)—" and insert -- OC(O)— --, therefor.

Column 13
Line 65, Delete "dimethyl m. isopropenyl" and insert -- dimethyl-m-isopropenyl --, therefor.

Column 14
Line 15 (Approx.), Delete "III.:" and insert -- III: --, therefor.

Column 17
Line 66, Delete "Uniquema" and insert -- Uniqema --, therefor.

CERTIFICATE OF CORRECTION (continued)
U.S. Pat. No. 8,440,779 B2

Column 18
Line 56, Delete "isostearylacohol" and insert -- isostearylalcohol --, therefor.

Column 19
Line 26 (Approx.), Delete "isostearylacohol" and insert -- isostearylalcohol --, therefor.

Column 20
Line 31, Delete "synsthesis" and insert -- synthesis --, therefor.